United States Patent
Bollati et al.

(10) Patent No.: US 9,999,706 B2
(45) Date of Patent: Jun. 19, 2018

(54) IMPLANTABLE DEVICES HAVING ANTIBACTERIAL PROPERTIES AND MULTIFUNCTIONAL SURFACES

(75) Inventors: Daniele Bollati, Brescia (IT); Marco Morra, Concesio (IT); Clara Cassinelli, Concesio (IT); Giovanna Cascardo, Concesio (IT)

(73) Assignee: NOBIL BIO RICERCHE S.R.L., Concesio (Brescia) (IT)

( * ) Notice: Subject to any disclaimer, the term of this patent is extended or adjusted under 35 U.S.C. 154(b) by 529 days.

(21) Appl. No.: 13/642,126

(22) PCT Filed: Mar. 24, 2011

(86) PCT No.: PCT/IB2011/051253
§ 371 (c)(1),
(2), (4) Date: Apr. 2, 2013

(87) PCT Pub. No.: WO2011/132096
PCT Pub. Date: Oct. 27, 2011

(65) Prior Publication Data
US 2013/0197660 A1 Aug. 1, 2013

(30) Foreign Application Priority Data
Apr. 22, 2010 (IT) .............................. MI2010A0688

(51) Int. Cl.
| A61L 27/20 | (2006.01) |
| A61L 27/34 | (2006.01) |
| A61L 27/24 | (2006.01) |
| A61L 27/26 | (2006.01) |
| A61L 27/52 | (2006.01) |
| A61L 27/54 | (2006.01) |

(52) U.S. Cl.
CPC .............. *A61L 27/34* (2013.01); *A61L 27/20* (2013.01); *A61L 27/24* (2013.01); *A61L 27/26* (2013.01); *A61L 27/52* (2013.01); *A61L 27/54* (2013.01); *A61L 2300/406* (2013.01)

(58) Field of Classification Search
None
See application file for complete search history.

(56) References Cited

U.S. PATENT DOCUMENTS

| 5,149,505 | A | * | 9/1992 | English ................... B01L 3/502 422/547 |
| 6,129,956 | A | * | 10/2000 | Morra et al. .................. 427/535 |
| 2005/0220837 | A1 | * | 10/2005 | Disegi et al. ................. 424/423 |
| 2005/0250939 | A1 | * | 11/2005 | Zhao ...................... A61L 27/20 536/53 |
| 2006/0286140 | A1 | * | 12/2006 | Wickstrom et al. .......... 424/423 |
| 2009/0263447 | A1 | * | 10/2009 | Asius .................... A61L 31/042 424/423 |

FOREIGN PATENT DOCUMENTS

WO    WO2010141133    * 12/2010 ............. A61L 27/40

OTHER PUBLICATIONS

Wright, Antibiotics: A new hope, Chemistry & Biology, 2012, vol. 19, pp. 3-10.*
Groot et al., Osteoinductive biomaterials-properties and relevance in bone repair, 2007, J. Tissue Eng., Regen Med. vol. 1, pp. 25-32.*
Hickok et al. (Antibiotic Modification of Native Grafts: Improving Upon Nature's Scaffolds, Tissue Engineering Part A, 2010, vol. 16, p. 2041-2049, publish online Mar. 17, 2010).*
Mehrotra, Infrared Spectroscopy, Gas Chromatograph/Infrared in Food Analysis, Encyclopedia of Analytical Chemistry, 2006, p. 1-16.*
Hiroaki Matsuno, Kazuo Yudoh, Masamichi Hasimoto, Yasukazu Himeda, Teruzo Miyoshi, Kaoru Yoshida, Syogo Kano, Antibiotic-Containing Hyaluronic Acid Gel as an Antibacterial Carrier: Usefulness of Sponge and Film-Formed Ha Gel in Deep Infection, Journal of Orthopaedic Research, Jan. 6, 2006, 321-326, vol. 24, No. 3, Wiley Inter Science, DOI 101002/jor.20070.
Helen F. Chuang, Renee' C.Smith and Paula T. Hammond, Polyelectrolyte Multilayers for Tunable Release of Antibiotics, Biomacromolecules, May 14, 2008,1660-1668, vol. 9, American Chemical Society, USA.
Yi Luo and Glenn D.Prestwich, Hyaluronic Acid-N-hydroxysuccinimide: A Useful Intermediate for Bioconjugation, Bioconjugate Chemistry, 2001, 1085-1088, vol. 12 No. 6, American Chemical Society.
Marco Morra, Biomolecular modification of implant surfaces, Expert Review of Medical Devices, Jan. 2007, 361-372, vol. 4 No. 3, Future Drugs Ltd., London.

* cited by examiner

*Primary Examiner* — Bethany P Barham
*Assistant Examiner* — Ping Cao
(74) *Attorney, Agent, or Firm* — Robert E. Alderson, Jr.

(57) ABSTRACT

Implantable devices having antibacterial activity for preventing periprosthetic infections and for improving osteointegration capacity are provided. Methods for making and using such devices are also provided.

5 Claims, 3 Drawing Sheets

IMPLANTABLE DEVICES HAVING ANTIBACTERIAL PROPERTIES AND MULTIFUNCTIONAL SURFACES

CROSS-REFERENCE TO RELATED APPLICATIONS

This application is a National Phase Application of PCT International Application No. PCT/IB 2011/051253, International Filing Date, Mar. 24, 2011, claiming priority to Italian Patent Application No. MI2010A000688, filed Apr. 22, 2010, both of which are hereby incorporated by reference in their entirety.

FIELD OF THE INVENTION

The present invention regards an implanting device whose surface combines antibacterial activity to prevent periprosthetic infections and improved osteointegration capacity.

BACKGROUND OF THE INVENTION

In orthopaedics, periprosthetic infection (PPI) is a devastating consequence of the insertion of implants. Currently the incidence of PPI ranges from 1 to 5%, with even greater values for high risk patients and for those that have suffered a trauma. Furthermore, about 73% of the operation reviews are carried out following a peri-implant bacterial infection. The social and economical cost of these interventions is considerably high. The etiology of PPI is complex and it depends on the ability of the bacterial species to elude the response of the host tissue, usually through the formation of a biofilm. Actually, once inserted, the implant device is coated by serum proteins. This process is followed by interactions with the cell species and the regeneration or reparation of the tissue in cases with positive course. In presence of bacterial species, the surface of the implant may be subjected to the bacterial adhesion and the formation of a biofilm. In particular, within the biofilm the bacteria are protected by the immune-surveillance system and by the effect of systemic antibiotics. In this manner, the colonization may propagate, with the harmful consequences known in the field of periprosthetic infection. A series of systems for the local release of antibiotics, both from cements and micrometric layers of biodegradable polymers deposited on the surface of the devices, were developed with the aim of fighting PPI. However, upon completing release, the porous systems of this type may serve as a protected site for the bacterial adhesion and the formation of biofilms.

Articles of literature have been recently presented in which an antibiotic, vancomycin, was covalently bonded to the surface of implant devices made of titanium and conducted bactericidal activity against bacterial species belonging to the Staphylococci genre (Chemistry & Biology, Vol. 12, 1041-1048, 2005, Vancomycin Covalently Bonded to Titanium Beads Kills *Staphylococcus aureus*; Journal Orthopedic Research, 25, 858-866, 2007, Vancomycin Covalently Bonded to Titanium Alloy Prevents Bacterial Colonization).

The immobilisation of vancomycin on the surface of implant devices or local release thereof are, for these applications, processes of great interest. Vancomycin constitutes a potent drug for treating Gram-positive bacterial infections, which are considerably the most common cause of periprosthetic infections. The action mechanism of vancomycin provides for the block of the synthesis of the layer of peptidoglycans of the gram-positive bacteria cell walls by means of L-Lys-D-Ala-D-Ala terminal bond of the nascent peptidoglycan. In this manner, vancomycin prevents the crosslinking which is required for the osmotic stability. The concept of firmly bonding vancomycin, per se water soluble, to the surface of the implant devices overcomes the vision of the simple release system. Actually, in this case there is a high local concentration of a drug firmly bonded to the interface between the implant device and the external environment. This stable pharmacological barrier prevents the formation of bacterial colonies on the surface of the implant device, thus preventing the occurrence of PPI. As described by Chapiro and collaborators in the article Selfprotective *Smart Orthopedic Implants*, Expert Rev. Med. Devices, 2007 January; 4(1):55-64, systems of this type can lead to a new generation of implant devices, which are self-protected against risks of bacterial infection due to their surface properties.

However, the process of bonding vancomycin to the surface of the device made of titanium described in these articles comprises different steps, which are quite complex from a practice point of view and not easily adaptable to industrial production, which makes it poorly suitable for devices of a given dimension and complex geometry.

Obviously, the provision, under conditions compatible with a productive context, of implant prosthetic devices capable of exploiting the pharmacological action of vancomycin would constitute a considerable step forward in the sector, with considerable scientific, social and economical implications. Ideally, the process could accompany the immobilization/release of vancomycin to provide other considerable surface properties, such as the increase of the osteointegration speed. Actually, the rapid regeneration of the bone tissue, with ensuing occupation of the available surface of the implanted device, reduces the probabilities of surface colonization by bacterial cells, completing the antibacterial protective effect due to vancomycin. This concept would allow the actual provision of devices with multifunctional surfaces, i.e. surfaces that perform, besides the obvious function of supporting the tissue components, also for example:

the function of stimulating the regeneration/reparation of the tissue the function of antibacterial protection.

Studies carried out by the present inventor have now revealed the possibility of practically implementing the previously mentioned concepts as described hereinafter.

SUMMARY OF THE INVENTION

The present invention regards the process for obtaining an implant device in the human or animal body capable of combining the immobilization of an antibiotic, in particular vancomycin, in a simple and efficient manner with the stimulation of the osteogenic cells and ensuing increase of the osteointegration speed. The rapid formation of bone tissue, with relative occupation of the available surface of the implanted device, reduces the probabilities of surface colonization by bacterial cells and thus constitutes a synergic effect with the antibiotic effect of vancomycin. According to the process subject of the invention, devices with multifunctional surfaces, i.e. surfaces that exert, besides the obvious function of supporting the tissue components, also the mentioned functions of stimulating the regeneration/reparation of the tissue and antibacterial protection, are thus provided for.

The present invention is based on the surprising observation that vancomycin, a water soluble compound, if present in an aqueous solution with the molecule of hyaluronic acid in presence of cross-linking/condensing agents, forms a compound/precipitate with said hyaluronic acid. From such observation, a process has been developed which replicates these events on the surface of implant devices. The process provides for, at the beginning, the bond of the molecule of hyaluronic acid to a suitably functionalised surface (with methods known in literature); then, the surface coated with hyaluronic acid is incubated in an aqueous solution of vancomycin in presence of cross-linking agents in suitable concentration. Surprisingly, there is gradually observed on the surface the formation of hyaluronic acid/vancomycin precipitates, observable also macroscopically due to the gradual formation of an "opaque" layer which homogeneously coats the entire surface, an event that does not occur if the surface was not previously coated with hyaluronic acid.

Without being restricted to a particular theory, it is deemed that this behaviour is at least partly due to the ionic interaction between the negative charges present in the molecule of hyaluronic acid and the positively charged amino groups of vancomycin. However, given that the formation of said opaque layer only occurs in presence of given cross-linking agents, the interaction could also be due to different physical and chemical factors, unexpectedly related to the molecular structure of the hyaluronic acid.

For the sake of brevity, in the present patent application such precipitates or compounds of a glycopeptide antibiotic, in particular vancomycin, and hyaluronic acid shall be defined "hyaluronic acid/glycopeptide antibiotic complexes" or specifically "hyaluronic acid/vancomycin complexes", without implying that the bond typical of a complex is necessarily formed.

Furthermore, it was surprisingly discovered that the use of different molecular weights of hyaluronic acid (HA) considerably influences the formation of said HA/vancomycin precipitate: in this case, it was observed that coating a surface with HA with low molecular weights (comprised between 5000 Da and 80000 Da) is not efficient at "capturing", in the subsequent treatment step, an amount of vancomycin molecules equivalent to that captured when the surface is coated with hyaluronic acid with higher molecular weight. Furthermore, the maximum yield in the capturing process does not increase as the weight of the hyaluronic acid increases, but it reveals a "peak" or bell development.

Furthermore, the use of other polysaccharides, among which heparin, chondroitin sulphate, chitosan, alginic acid, pectins, has the effect of reducing the amount of functional vancomycin which is bonded on the surface (in some cases reducing stability thereof, in others the pharmacological activity).

Surprisingly, the compound/precipitate incorporated in the surface layer is released if exposed to physiological aqueous environments, preserving the pharmacological action of vancomycin. The total release of vancomycin is not immediate, as it would be expected due to the high solubility of vancomycin in aqueous solutions, but the effect remains for several weeks, offering an extended interfacial antibiotic coating.

Hyaluronic acid is deposited on the surface of the device to be coated using different methods that allow pre-treating the surface to be coated with allylamine plasma or polyethyleneimine aqueous solution, with amino groups capable of allowing covalent bonding with the carboxyl groups of the hyaluronic acid.

According to a preferred embodiment, the surface to be treated can be coated with a single layer of collagen molecules, preferably in fibrillated forms: the amino groups of the amino acid residues of the collagen molecule are capable of bonding the carboxyl groups of hyaluronic acid. The functionalization of the surfaces with collagen also allows increasing the "osteoinductive" properties of the surface: actually, it was observed that such modification is capable of directing the differentiation of human mesenchymal cells towards the osteogenic line.

The previously described process is versatile and it is not limited by the type of the device. It can thus be applied both on metal devices such as screws made of titanium for fixing fractures, for prosthesis, on polymeric devices, both biodegradable and permanent, and on ceramic devices, for example hydroxyapatite or other forms of calcium phosphates, even in form of particulate like powders and granules as used for void bone fillers.

The process of the invention may be applied on shaped bodies based on natural materials such as sponges or scaffolds based on collagen or natural polymers or ceramic materials. It can also be applied to suspensions of nanostructured organic material, such as collagen fibrils with diameter smaller than a micron.

In case of application to collagen suspensions or nanostructured materials in suspension, the interaction subject of this invention leads to the formation of a gel. This gel—based on collagen and containing vancomycin and hyaluronic acid—can be used, as it is or in lyophilized forms and reconstituted when using, as filling material in the site of fixation an implantable device, performing both the typical action of osteointegration of collagen and hyaluronic acid and the antibacterial activity of the antibiotic also in the region surrounding the implant.

Thus, these processes allow providing a vancomycin coating in hyaluronic acid on the surface of the devices or materials, implementing the concept of slow release pharmacological barrier to the device/tissue interface. Furthermore, the surface modification of implant devices with hyaluronic acid increases the tendency of the material to osteointegration, as described for example by Morra et al. in the article Covalently-Linked Hyaluronan Promotes Bone Formation around Ti Implants in a Rabbit Model, published on the Journal of Orthopedic Research, 27:657-663, 2009 and in the patent application WO2006/038056 A1.

Thus, the previously described methods allow providing implant devices that do not only have optimal and improved osteointegration characteristics but they also provide the self-protective and bactericidal characteristics of vancomycin, practically translating the concept of multifunctional surface. Furthermore, the method of the present invention allows extending the multifunctionality of the surface, exemplified by the simultaneous presence of the bioactive chemical composition with osteogenic action (hyaluronic acid bond) and pharmacological action (release of vancomycin), adding the possibility of controlling the surface topography through roughening processes. Regarding this, it should be borne in mind that in the field of dental implants the osteointegration process is facilitated by the action of the surface topography on the osteogenic cells, as exemplified by the concept of "Modulation of osteogenesis via implant surface design", described by Boyan, B. D., Schwartz, Z., in: Davies J. E. editor. Bone Engineering, Toronto, em squared, 232-239, 2000. This concept has been so successful to a point that dental implants with smooth surface are no longer available in the market all having instead a rough surface topography. In orthopaedics, for example in the fixation of fractures by means of screws made of titanium, this concept could not be exploited due to the fear of offering, by roughening the surface, surfaces that can be exploited for bacterial adhesion and colonization. The present invention instead allows providing a conformal hyaluronic acid surface osteogenic layer (i.e. which does not alter the topography of the surface, adapting thereto), which can also exploit the roughening of the surface topography in that the release of vancomycin prevents the bacterial colonization of the unevenness and roughness of the surface.

Figure 1:
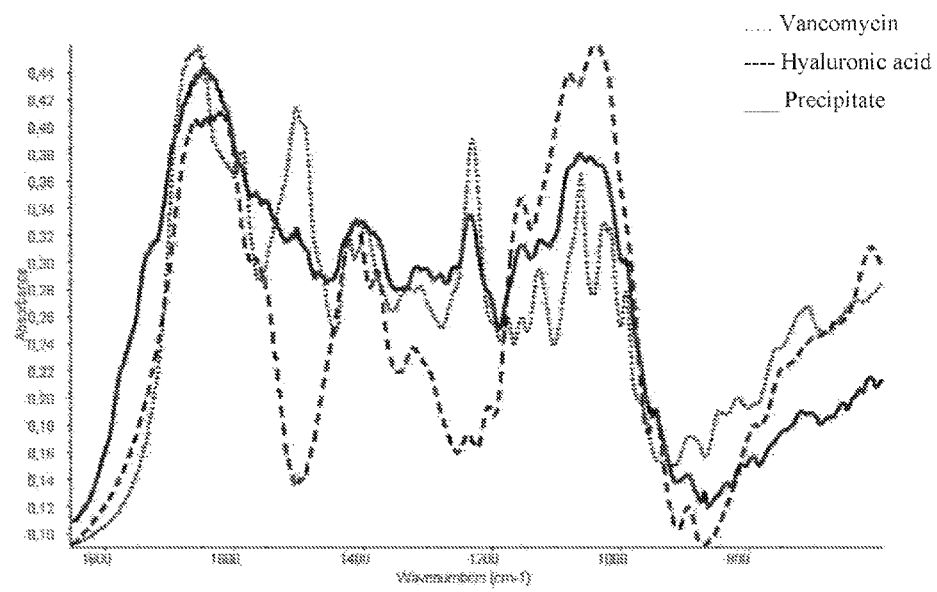
FIG. 1 shows the IR spectra for vancomycin (dots), hyaluronic acid (dashes) confirming interaction between the two molecules.

The present invention regards in particular an implanting device in the human or animal body, in which at least one part of the surface of said device is coated with a hyaluronic acid compound with a glycopeptide antibiotic.

In an embodiment, the glycopeptide antibiotic is vancomycin.

The idea is to bond a layer of hyaluronic acid to the surfaces of interest (through the methods known in the art), then incubate such surfaces with a solution of vancomycin in presence of condensing agents, in particular N-hydroxysuccinimide (NHS) and 1-ethyl-3-(3-dimethylaminopropyl) carbodiimide (EDC), present simultaneously: an "opaque" layer, indicating the interaction between the previously bonded hyaluronic acid and vancomycin is formed on the surface after a few hours. This opaque layer is not formed in the absence of hyaluronic acid bonded to the surface, functionalised or non-functionalised, and it is not formed in absence of NHS/EDC. From now henceforth, reference shall be made to "hyaluronic acid complexes with vancomycin", where the term "complex" comprises any type of chemical/physical or simply physical interaction between hyaluronic acid and vancomycin, including hydrogen bond interactions, and/or Van der Waals interactions and/or electrostatic interactions etc, which is obtained through the precipitation of vancomycin or co-precipitation of hyaluronic acid and vancomycin in presence of cross-linking or condensing agents and in particular conditions (pH and concentration of the solutions).

In an embodiment, the entire surface of the implanting device is coated with said hyaluronic acid/glycopeptide antibiotic complex bonded to the surface having a. Alternatively, part of the device is coated with hyaluronic acid, and the formation of the complexes with vancomycin only occurs in this area.

The implanting device according to the invention can be made of metal (for example, steel, titanium or alloys thereof with other metals) or made of plastic material (such as for example polystyrene) compatible for applications on the human or animal body, or made of ceramic material, both in form of the device and granulate/powder.

In an embodiment, the device consists of a dental implant screw, preferably made of titanium or alloys thereof, possibly of the transmucosal type, or a screw, preferably made of titanium or alloys thereof, for spinal or skeletal fixation, or for fracture fixation, or an intervertebral disc, preferably made of titanium, alloys thereof or cobalt-chromium alloys or made of metal alloys commonly used for these applications. The surface of the device made of titanium can be smooth (commonly referred to as "machined") or preferably roughened according to methods known in the art, in particular through sand blasting, using alumina, titanium oxides or other sand blasting agents, roughening treatment using acids, or electrochemical roughening treatment.

In an embodiment, the process of immobilizing the hyaluronic acid complex with the glycopeptide antibiotic on an implantable device according to the invention provides for the introduction of functional amino groups on the surface of the device. Hyaluronic acid is bonded covalently to the surface amino groups, through the methods known in the art, and exerts the vancomycin "capturing" action thereof with formation of the complexes in presence of EDC and NHS in the next step. The average molecular weight of hyaluronic acid may be comprised between 4.000 and 4 million Da, preferably between 400,000 and 1 million Da. The bond of hyaluronic acid to the amined surface may occur through the methods known in the art, for example by using EDC/NHS, or by treating hyaluronic acid with periodate acid and subsequent reductive amination, or as described in WO2006/038056 A1. The layer thus obtained may have a thickness comprised between 0.1 and 1000 nanometres, preferably between 1 and 20 nm.

The amino groups may be deposited on the surface of the implantable device according to the methods widely known in the sector. The technique which provides for the introduction of the substrate having functional amino groups on the surface of the implantable device through plasma deposition of molecules carrying the amino groups is particularly advantageous. Typical examples of molecules used for this purpose are allylamine, alkylamines such as hexylamine or heptylamine and, generally, organic molecules having amino functions which exhibit the required volatility characteristics in the plasma state. The plasma deposition of amine occurs in the following conditions: pressure comprised between 80 and 300 mTorrs, discharge power comprised between 5 and 200 W, deposition time between 1 ms and 300 s. Plasma deposition may also occur in pulsed plasma conditions, with active and inactive plasma cycles comprised between 1 and 100 ms, to minimize the molecular fragmentation and maintain the highest density possible of the amino groups. The plasma deposition treatment of amines may be preceded by other plasma treatments, for example using air or oxygen plasma for cleaning the surface and increasing adhesion with the substrate.

A further method for coating the implantable device with a substrate containing amino groups consists in adsorbing polyethyleneimine (PEI) on the device surface, for example from a 0.2% aqueous solution, for 2 hours, at ambient temperature. Also the use of silanes, for example 3-aminopropyltriethoxysilane (APTES), or analogous compounds, falls within the common methods of surface functionalization.

It is also possible to functionalise the surface of the implantable device with carboxyl groups through plasma deposition of acrylic/methacrylic acid.

Furthermore, it is possible to functionalise the surface with natural molecules, possibly bioactive, which are irreversibly adsorbed on the surface and have amino/carboxylic groups suitable for the subsequent bond of hyaluronic acid and complexes thereof with vancomycin. Typical examples falling within this category are collagen and other extracellular matrix protein molecules, such as laminin, fibronectin, vitronectin. According to this embodiment, the implanting device according to the invention comprises a first layer of adsorbed collagen, in a monomer or fibrillated form, to which hyaluronic acid is bonded, according to the described process, preferably through EDC/NHS, or through reductive amination. This is followed by the formation of the hyaluronic acid/vancomycin complexes, through exposure to vancomycin and cross-linking or condensing agents solutions. The functionalization with collagen is preferably performed with a 0.3% collagen solution in 10 mM acetic acid and an equal volume of phosphate buffer at 37° C. for 8 hours.

The previously described method may also be performed on collagen in suspension, leading to the formation—in the aqueous medium—of a precipitate of complex of fibrillated collagen, hyaluronic acid and glycopeptide antibiotic (such as vancomycin), which can be separated, washed and partly dried to obtain a gel. This gel based on collagen and containing said glycopeptide antibiotic and hyaluronic acid can be used, as it is or in lyophilized forms and reconstructed when using, as filling material in the site of fixation of said implantable device, performing both the typical osteointegration action of collagen and hyaluronic acid as well as the antibacterial activity of the antibiotic also in the region surrounding the implant.

A further object of the invention is a kit comprising an implanting device on the human or animal body, in which at least one part of the surface of said device is coated with a hyaluronic acid complex with a glycopeptide antibiotic, and a fibrillated collagen gel with said hyaluronic acid/glycopeptide antibiotic complex.

The following examples describe the invention.

EXAMPLE 1

Hyaluronic Acid-vancomycin Interaction

This example shows that there is a surprising interaction between vancomycin and hyaluronic acid.

A 0.1% (w/v) solution of hyaluronic acid HW (molecular weight 800 kDa, Lifecore) in milliQ water and a 0.5% vancomycin solution in milliQ water is prepared. The hyaluronic acid solution is gradually added to the latter solution and a gradual increase of the turbidity of the solution up to the formation of particles in suspension is observed (sign of strong interaction between HA and vancomycin). If two condensing agents, N-hydroxysuccinimide and subsequently ethyl-carbodiimide are added to the mixture, the solution turns instantly limpid. However, after 15 hours, the mixture becomes very turbid, with the presence of precipitates in suspension: probably the condensing agents are capable of bonding the amino groups of vancomycin to the carboxyl groups of the hyaluronic acid. Such precipitates were collected, washed with milliQ water and subsequently analysed under IR: FIG. 1 shows the spectra relative to vancomycin (dots), hyaluronic acid (dashes) and the precipitate formed through the described method (continuous). In this spectrum there are signals of vancomycin and signals of hyaluronic acid, confirming interaction between the two molecules.

EXAMPLE 2

Hyaluronic Acid-vancomycin Interaction

This example shows the fundamental role of condensing agents in the interaction between vancomycin and hyaluronic acid.

The previous experiment is repeated using hyaluronic acid and vancomycin solutions at very low concentrations (up to 10 times lower): in these cases, the addition of hyaluronic acid to a vancomycin solution does not cause an immediate turbidity of the mixture, which remains limpid. However, by adding the same amounts of condensing agents used in the previous experiment and leaving in incubation for about 15 hours, the solution turns turbid (even though at a lower degree with respect to the large precipitates formed in the previous experiment), proving that the HA-vancomycin interaction is somehow "stimulated" by the presence of condensing agents.

Solutions with high concentration of vancomycin in water (1%) and HA in water (0.5%) were prepared with the aim of observing possible differences between the HA-vancomycin interaction that occurs in presence or in absence of condensing agents. Such solutions were mixed and the precipitate immediately formed was collected, washed and analysed under IR. The spectrum relative to this precipitate was then compared with that relative to the precipitate that is formed in presence of condensing agents.

Figure 2:
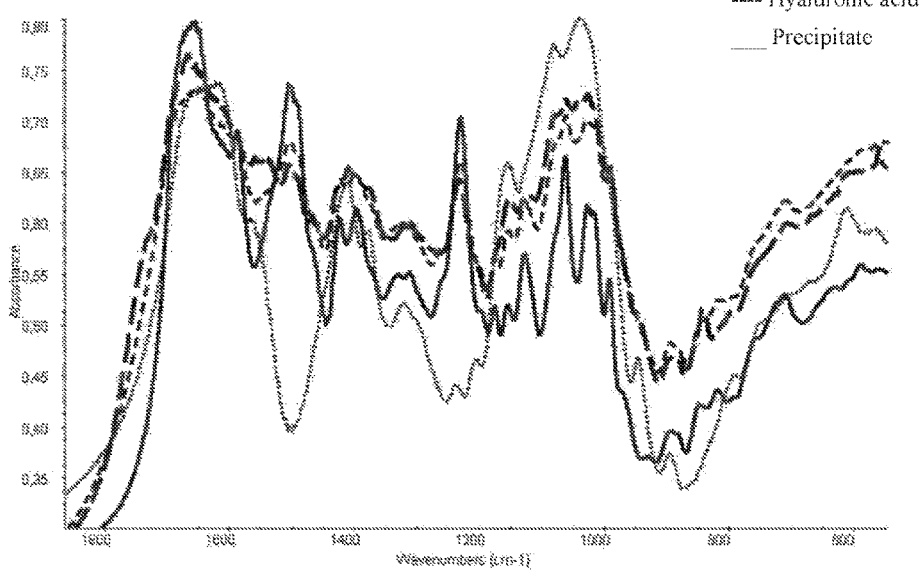
FIG. 2 shows—through dotted and solid lines—the IR spectra of HA and vancomycin respectively, while the long dash line shows the IR spectrum of the HA-vancomycin precipitate in presence of condensing agents and the short dash line shows the IR spectrum of the precipitate in absence of condensing agents.

FIG. 2 shows—through a dotted and solid line—the spectra of HA and vancomycin respectively, while the long dash line shows the spectrum of the HA-vancomycin precipitate in presence of condensing agents and the short dash line shows the spectrum of the precipitate in absence of condensing agents.

There are two important signals present in the spectrum in long dash line and not in the short dash line: the first is at 1550 cm-1, which could be the signal of the secondary amide (bending NH2 and stretching CN); the second is at 840 cm-1 and it could be the signal of aliphatic amines and the bending OCN. These two signals, solely present in the spectrum of the precipitate formed in presence of condensing agents (but not actually belonging to the condensing agents), could indicate that bonds different from those deriving from simple electrostatic interaction, such as covalent bonds, specific interactions or other interactions formed in such precipitate.

Potential existence of a strong interaction between hyaluronic acid and vancomycin has paved the way towards new surface modification experiments. Such experiments consist in covalently bonding hyaluronic acid to a suitably functionalized surface, then incubating the abovementioned surface in a solution of vancomycin in presence of condensing agents, so as to directly provide the same reaction observed in the solution on the surface.

EXAMPLE 3

HA-vancomycin Interaction on a Surface

This example shows that the process observed in solution also occurs directly on the surface of a material.

Polystyrene surfaces were prepared as follows:
air plasma treatment for 20 seconds
incubation with Polyethyleneimine solution (PEI) 0.5% in water for 2 hours
washing with milliQ water (3 times)
incubation of the polystyrene surfaces O.N. with hyaluronic acid solution 800 kDa 0.2% (Lifecore) in milliQ water, in presence of 5 mg/cc NHS and 7.5 mg/cc EDC.
washing with milliQ water (2 times)
incubation with 0.7% vancomycin solution in water overnight, in presence of 5 mg/cc NHS and 7.5 mg/cc EDC.
Washing with milliQ water (3 times)

At the end of the treatment on the polystyrene surfaces thus prepared a very homogeneous opaque thin layer, derived from the occurred interaction between hyaluronic acid bonded on the surface in the first reaction step and the vancomycin added in the second reaction step is observed. Polystyrene surfaces treated in the same manner but in absence of NHS and EDC during the second incubation in vancomycin solution, are perfectly transparent hence confirming the importance of the condensing agents.

EXAMPLE 4

Process for Coating an Implant Screw Made of Titanium with Hyaluronic Acid and Vancomycin Some implant screws made of titanium, with a length of 13 mm and width of 4 mm, are treated as follows:
sample 1: no treatment (Ti sample)
sample 2: surface functionalization using PEI, and HA bonding like in example 3 (Ti-HA Sample).
sample 3: a sample treated like in point 2 was subsequently subjected to incubation with a 0.7% vancomycin solution in water overnight, in presence of 5 mg/cc NHS and 7.5 mg/cc EDC and subsequent washing with milliQ water (Ti-HA-VXL sample)

The samples thus obtained were subsequently subjected to XPS (X-ray Photoelectron Spectroscopy) analysis to evaluate the chemical composition of the surface. A sample of vancomycin, obtained by leaving a solution of vancomycin in milliQ water to evaporate on a plastic substrate was analysed therealong as reference. The following results were obtained, expressed in percentage of atoms and reminding that the XPS analysis does not measure the presence of hydrogen atoms:

| Sample | C | O | N | Ti | Cl |
|---|---|---|---|---|---|
| Vancomycin | 77.8 | 15.9 | 4.6 | | 1.7 |
| Ti | 34.8 | 46.4 | 0.4 | 18.4 | |
| Ti-HA | 69.0 | 24.4 | 6.3 | 0.3 | |
| Ti-HA-VXL | 69.5 | 23.2 | 5.8 | 0.6 | 0.9 |

The vancomycin molecule is characterised, for analytical purposes regarding this evaluation, by the presence of the Cl hetero-element (two atoms in a compound also comprising O, C and N with molecular weight of about 1450 Da). The presence of Cl, at an atomic percentage lower than 2%, is actually shown by the XPS analysis, as indicated in the table, in the line indicating the analysis of Vancomycin. The surfaces of the Ti screw and of the Ti-HA screw are characterised by composition values in line with the expectations, as observable from the literature of the sector.

The composition of the surface of the Ti-HA-VXL sample is different from that of Ti-HA due to the presence of Cl, hence the introduction of the Vancomycin molecule on the surface.

EXAMPLE 5

Example of the Importance of the Molecular Weight of Hyaluronic Acid on the Release of Vancomycin from Surfaces Modified Through the Present Process Modified polystyrene surfaces with different molecular weights of HA and then with the vancomycin solution in presence of NHS and EDC were prepared to observe the specificity of the HA-vancomycin reaction. HA LW (10 kDa), HA MW (about 70 kDa), HA HW (880 kDa) and HA HHW (about 2000 kDa) were used. Thus, the surfaces were first functionalised with polyethyleneimine (0.5% solution in water for 2 hours); then incubation was conducted overnight with the HA solutions with different molecular weight in presence of NHS and EDC. Washing was subsequently carried out in water and then the surfaces were incubated overnight with a 0.8% vancomycin solution in water in presence of 5 mg/ml NHS and 7.5 mg/ml of EDC.

The opacity of the surface was observed solely with the HA HW weight, even though for HA MW and HA HHW the wells did not appear perfectly transparent: thus, there is a certain specificity, even though only dimensional, in the interaction between vancomycin and HA HW.

Figure 3:
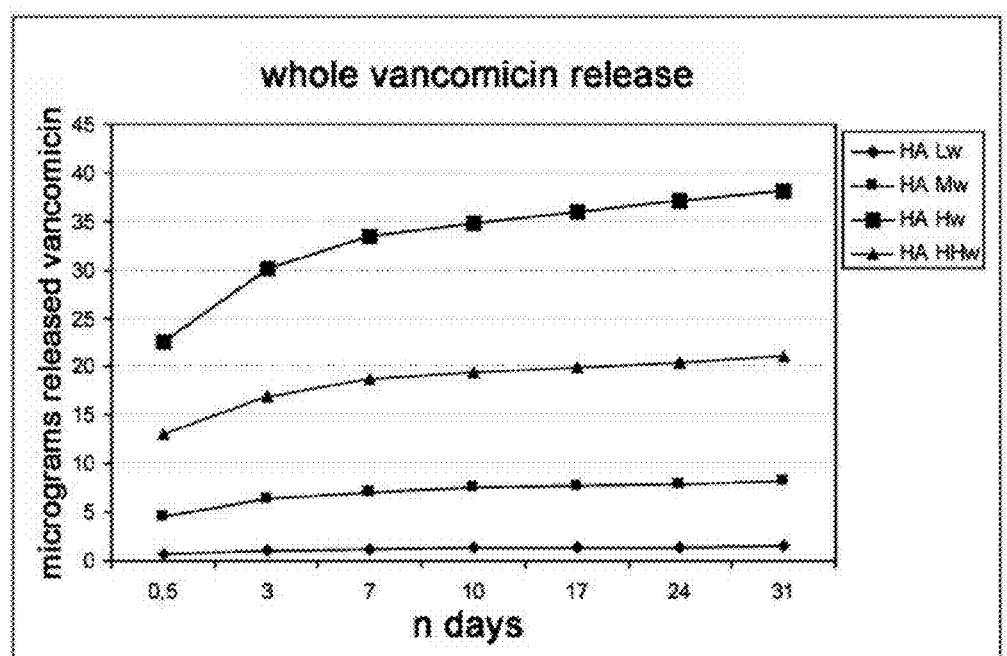
FIG. 3 shows the amount of vancomycin released by the different surfaces over time (one month).

At the end of the washing, the surfaces were incubated in PBS to conduct the analysis of vancomycin release over time through HPLC. The chart in FIG. 3 shows the amount of vancomycin released by the different surfaces over time (one month): it can be observed that the surface modified with HA HW releases a greater amount of antibiotic with respect to those modified with the other molecular weights.

EXAMPLE 6

Influence of the Functionalization Process on the Amount of Vancomycin Released by Surfaces Modified Through the Present Process The treatment of two 6-wells of polystyrene with HA+VXL (VXL=Vancomycin and condensing agents EDC-NHS), but functionalizing the surfaces with PEI (polyethyleneimine) or with fibrillated collagen was planned to verify whether functionalization with fibrillated collagen causes some changes in the rate of releasing vancomycin from the polystyrene surfaces. The 6-wells were plasma treated like in the previous example, then the wells were incubated with a solution of PEI 0.5% in water for 2 hours or with a 0.3% collagen solution in 10 mM acetic acid and an equal volume of PBS a 37° C. for 8 hours.

Before the step of functionalizing, the surfaces were treated with a 0.2% HA HW solution in presence of NHS and EDC overnight, then washed with milliQ water and incubated with a 0.75% vancomycin solution in water in presence of NHS and EDC overnight. At the end of such incubation, the surfaces were washed with milliQ water and dried.

Figure 4:
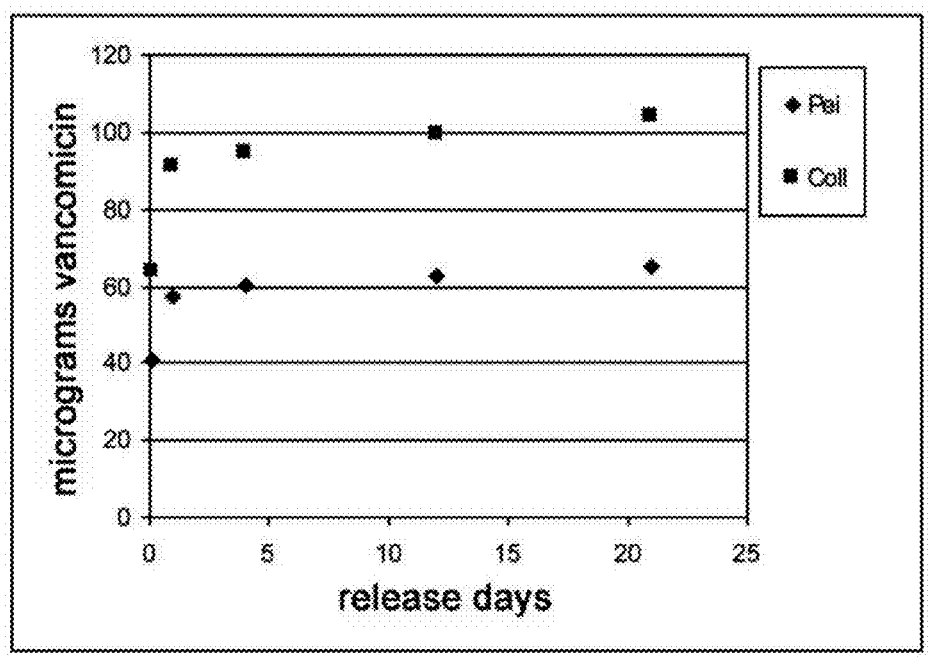
FIG. 4 shows the cumulative curve of the release of vancomycin from the differently functionalised surfaces.

Releasing step was conducted in PBS at 37° C., with the measurement of the amount released at 4 hours, 24 hours, 4 days, 12 days and 21 days through HPLC. All the times revealed that the surfaces modified with collagen release a greater amount of antibiotic with respect to those functionalised with PEI. The chart in FIG. 4 shows the cumulative curve of the release of vancomycin from the differently functionalised surfaces: it can be observed that, at each time point, the surfaces functionalized with fibrillated collagen release a greater amount of vancomycin.

This example indicates that, for surprising and not entirely clear reasons, the surface functionalization step, in particular the molecular species used for the surface functionalization, influences the total amount of vancomycin "captured" from the surface coated with hyaluronic acid and/or the amount of vancomycin that the surface coated with hyaluronic acid is capable of releasing. Going beyond the importance of this observation from an applicative point of view, the result confirms that the observed phenomenon is not a general effect of the action of EDC-NHS on the vancomycin in solution, but it is bonded in a surprising and unexpected manner to the molecular structure of the surface.

EXAMPLE 7

Verifying the Improved Properties of Stimulation of the Osteogenic Behaviour of Mesenchymal Cells In order to evaluate the response of the mesenchymal cells to the coating process and thus verifying whether the latter can also have effects on osteogenesis, mesenchymal cells were cultured on the following surfaces, provided on plates with micro-wells for cellular cultures:
  plastic for cellular cultures (control)
  plastic for cultures functionalised with PEI and subsequent covalent bond of hyaluronic acid 800 kDa (HA)
  plastic for cultures functionalised with PEI and subsequent covalent bond of hyaluronic acid 800 kDa, followed by the formation of HA-Vancomycin complexes as described in the previous example (HA-VXL)

Mesenchymal cells from human bone marrow were acquired from Lonza Milano srl in undifferentiated form. As known, according to external stimuli, these cells can differentiate along some different paths, including the osteogenic one. The cells were cultured in an osteogenic medium and the expression of some genes responsible for the formation of bone tissue thereof was evaluated through Real Time Polymerase Chain Reaction (RT-PCR) analysis. The data are reported in the following table, where "=" means expression equivalent to that of the control, "+" expression up to 5 times greater than that of the control, "++" expression greater than 5 times that of the control.

The following results were obtained, after 10 days of culture:

| Gene | HA | HA-VXL |
|---|---|---|
| Alkaline phosphatase | = | + |
| RunX2 | + | + |
| Osteocalcin | + | + |
| Bone Sialoprotein | ++ | ++ |
| Bone Morphogenetic protein -2 (BMP-2) | ++ | ++ |

These data confirm that coating with HA stimulates the expression of genes linked to the formation of bone tissue, confirming the in vivo data cited in literature regarding the effect of the covalent bond of surface layers of HA on osteointegration (Morra et al. Covalently-Linked Hyaluronan Promotes Bone Formation around Ti Implants in a Rabbit Model, published on the Journal of Orthopedic Research, 27:657-663, 2009). In particular, both the RunX2 transcription factor, which controls the cellular differentiation, and in particular the BMP-2 protein and the BSP (Bone Sialoprotein) are markedly over-expressed on HA and HA-VXL with respect to the control, and they indicate an extremely significant osteogenic process. The presence of the complexes with vancomycin does not substantially alter the advantages of HA (on the contrary, another very important gene, alkaline phosphatase, appears more expressed on HA-VXL with respect to HA), confirming that also this type of surface is pro-osteogenic. This is a very important property, which combined with the peculiar release of the antibiotic, is at the base of the generation and design of multifunctional devices.

EXAMPLE 8

Figure 5:
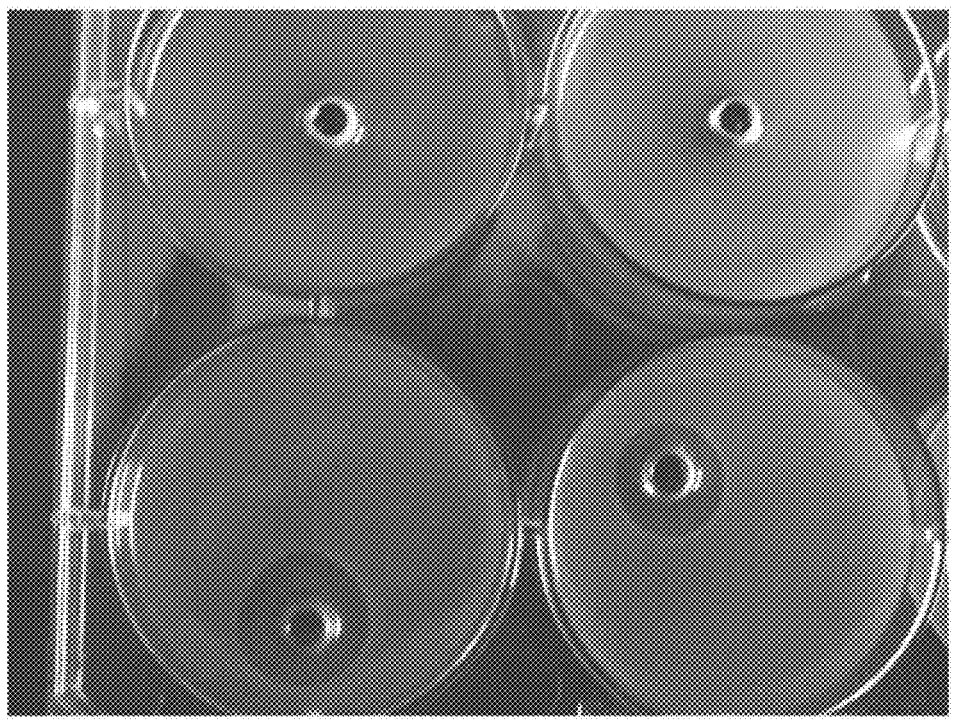
FIG. 5 shows control implants at the top (only titanium on the left, Ti coated with HA on the right) and treated implants at the bottom (HA-VXL, two replicas), around which the inhibition areola is clearly observable.

Verification of the Antibacterial Efficiency of Implant Screws Obtained According to the Present Process Inhibition areola tests were conducted in *Staphylococcus epidermidis* cultures with the aim of proving the antibacterial action of the present invention. Implants coated with HA and with HA-VXL are provided through the methods described previously. These implants, alongside the negative control ones (untreated implants), were then incubated in a semi-solid agar medium together with the bacterial mixture in a Petri dish at 37° C. The bacteria should proliferate and, in the case of a surface with antibacterial properties (with release of antibiotic), an inhibition areola, i.e. an area without bacteria surrounding the implant, should form around the implant. The results of this experiment confirmed that the developed treatment has antibacterial activities: actually, around the HA+VXL implants the inhibition areola, which is not formed around the control implants, is observed. FIG. 5 represents a picture explaining the experiment, with the control implants at the top (only titanium on the left, Ti coated with HA on the right) and the treated ones at the bottom (HA-VXL, two replicas), around which the inhibition areola is clearly observable.

The implants thus treated were subsequently collected and once again submerged into an agar containing bacteria to verify whether they would maintain their antibacterial activity: actually, the inhibition areola forms around the treated implants also in this second incubation, even though having a diameter slightly smaller with respect to the one formed the first time. The same happened also in the case of a third incubation.

Thus the surfaces of the HA-VXL implants reveal the greater osteogenic characteristics of hyaluronic acid, as shown by the example 7, with which the antibacterial properties revealed by the results exemplified by the photograph indicated in FIG. 5 are combined. Thus, this example confirms the multifunctional nature of the surface obtained according to the present process, and the applicative advantage thereof both with respect to the conventional device (screw made of titanium) and with respected to the device coated with HA described in the art.

EXAMPLE 9

Embodiment of a Fracture Fixation Screw Made of Titanium, with Roughened Surface and Coating with Hyaluronic Acid-vancomycin A screw made of titanium degree 5 for fracture fixation is used for the demonstration of the preparation of an implant device with multifunctional surface, having the following properties:

rough surface and ensuing increase of surface area bioactive surface through hyaluronic acid bond upon functionalization through adsorption of fibrillated collagen antibacterial surface through the release of the vancomycin present in complexes with hyaluronic acid bonded to the surface.

The apical portion (head) of the screw is produced through masking and the screw is subjected to a sandblasting process for 40 seconds in a Norblast sandblasting machine, using titanium oxides as sanding agent. The screw is then subjected to a treatment process with acids, according to protocols commonly used by this company to treat dental implants and then subjected to the process in question like in example 7 and 8.

The roughened surface of the screw has a surface area, and thus a contact surface, more than 70% greater than that of a conventional screw.

It is obvious that only some particular embodiments of the present invention have been described and they can be subjected—by a man skilled in the art—to any modifications required for adaptation thereof to particular applications without departing from the scope of protection of the present invention.

The invention claimed is:

1. A coating for an implant device for a human or animal, the coating comprising an opaque precipitate which comprises a reaction product of hyaluronic acid, vancomycin and a condensing and/or cross-linking agent,
   wherein the hyaluronic acid has an average molecular weight between about 400,000 and about 1,000,000 Da.

2. The coating of claim 1, wherein the condensing or cross-linking agent comprises N-hydroxysuccinimide and 1-ethyl-3-(3-dimethylaminopropyl) carbodiimide.

3. An implant device for a human or animal comprising a coating which comprises an opaque precipitate which comprises a reaction product of hyaluronic acid, vancomycin and a condensing and/or cross-linking agent wherein the hyaluronic acid has an average molecular weight between about 400,000 and about 1,000,000 Da.

4. The device of claim 3, comprising material selected from the group consisting of: steel, titanium, alloys of steel, alloys of titanium, ceramic materials and combinations thereof.

5. The device of claim 3, wherein said device is a screw comprising material selected from the group consisting of: titanium, alloys of titanium, cobalt-chromium, alloys of cobalt-chromium and combinations thereof.

* * * * *